United States Patent [19]

Holtsch

[11] Patent Number: 5,477,761
[45] Date of Patent: Dec. 26, 1995

[54] DEVICE FOR DISPENSING BANDAGES

[75] Inventor: Peter Holtsch, Taunusstein/Wingsbach, Germany

[73] Assignee: Holtsch Metallwarenherstellung, Taunusstein, Germany

[21] Appl. No.: 431,110

[22] Filed: Apr. 28, 1995

Related U.S. Application Data

[63] Continuation-in-part of Ser. No. 155,454, Nov. 19, 1993, abandoned.

[51] Int. Cl.$^6$ ...................................................... B26D 1/06
[52] U.S. Cl. ............................... 83/221; 83/276; 83/399; 83/455; 83/614; 83/649; 83/699.11; 83/699.31; 83/955; 30/339
[58] Field of Search ........................... 83/221, 276, 399, 83/455, 614, 649, 734, 207, 277, 279, 282, 699.11, 699.31, 699.51, 955; 225/52, 85; 30/339

[56] References Cited

U.S. PATENT DOCUMENTS

| 774,314 | 11/1904 | Ebert et al. | 225/52 |
|---|---|---|---|
| 1,249,221 | 12/1917 | Skeen | 83/399 X |
| 2,251,823 | 8/1941 | Cullen | 225/52 |
| 2,792,885 | 5/1957 | Greene | 83/221 X |

FOREIGN PATENT DOCUMENTS

| 2201396 | 7/1973 | Germany. |
|---|---|---|
| 2542713 | 3/1977 | Germany. |
| 2755921 | 6/1979 | Germany. |
| 9200572 | 4/1992 | Germany. |
| 292879 | 6/1928 | United Kingdom. |
| 2088825 | 6/1982 | United Kingdom. |

Primary Examiner—Richard K. Seidel
Assistant Examiner—Raymond D. Woods
Attorney, Agent, or Firm—Michael J. Striker

[57] ABSTRACT

A device for dispensing a bandage material has a container for accommodating a supply of bandage material, a mechanism for advancing the bandage material from the container so as to expose a desired portion of the bandage material outside of the container, a mechanism for cutting the exposed piece of the bandage material, and including a cutting element movable between an initial position before cutting the piece of the bandage material and a final position after the piece of the bandage material has been cut off during which movement from the initial position to the final position the piece of the bandage material is being cut, and a structure for preventing advancement of the bandage material by the advancing mechanism when the cutting element is in the final position.

13 Claims, 5 Drawing Sheets

DEVICE FOR DISPENSING BANDAGES

This application is a continuation-in-part of application Ser. No. 08/155,454 filed Nov. 19, 1993, abandoned.

BACKGROUND OF THE INVENTION

The present invention relates to a device for manual dispensing of bandages and the like. Bandages are well known covering wounds and other injuries. The bandages are usually manufactured and sold in certain predetermined sizes and they cannot be easily adjusted during use to specific sizes of wounds and the like. It is therefore advisable to provide a manual device, with which a user can dispense from a bandage supply a bandage piece with a size exactly corresponding to the size of the wound to be covered, Such a device is disclosed in my German patent document G9200572.1. This device contains a roll of bandage material, means of advancing the bandage material from the roll so as to expose a bandage piece of a desired size, and means for cutting the exposed piece. This device can be further improved.

SUMMARY OF THE INVENTION

Accordingly, it is an object of the present invention to provide a device for dispensing bandages which is a further improvement of the existing device.

In keeping with these objects and with others which will become apparent hereinafter, one feature of the present invention resides, briefly stated, in a device for dispensing bandages and the like which has a container for accommodating a supply of bandage material, means for advancing the bandage material so as to expose from the container a desired piece of the material, and means for cutting the exposed portion wherein the means for cutting includes a cutter movable from an initial position to a final position for cutting the bandage portion, and additional means for blocking the advancement of the bandage material from the container when the cutting element is in its final position.

In such a construction the bandage material cannot be advanced unless the cutting element is returned to its initial position from which it can move and cut the bandage material. Otherwise, if in a known device the cutter is located in its final position and the bandage material is advanced to be exposed outside, then when the user moves the cutter from the final position, no cutting can be performed and the bandage material is just misplaced.

In accordance with another feature of the present invention, the cutting means include a cutter holder with a stationary part and a removable part designed so that by simply pushing the cutter, the removable part together with the cutter can be removed from the stationary part and then the cutter is turned so as to expose another non-worn cutting edge for cutting a bandage material. Thus, when one cutting edge of the cutter is worn, the cutter can be easily reversed and the opposite cutting edge can be used to perform cutting.

Still another feature of the present invention is that means is provided for reliably holding the bandage material during cutting, which means include springy projections formed on a guiding wall which guides the cutting element, so that when the cutting element moves from its initial position to its final position the guiding wall is displaced towards the exposed bandage material to clamp it during cutting and when the cutting element is moved back to its initial position the springy projections move back the guiding wall to allow subsequent advancement of the bandage material.

In addition, in order to improve the holding of the bandage material during cutting, the surface of the guiding wall which faces the bandage material is provided with a plurality of small, tooth-like projections which engage and clamp the bandage material during cutting.

In accordance with a further feature of the present invention, two cams can be provided in the channel to keep the bandage material up in the right position and to avoid its falling back. Also, instead of the cams other formations for example springs can be provided and formed as barbs.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
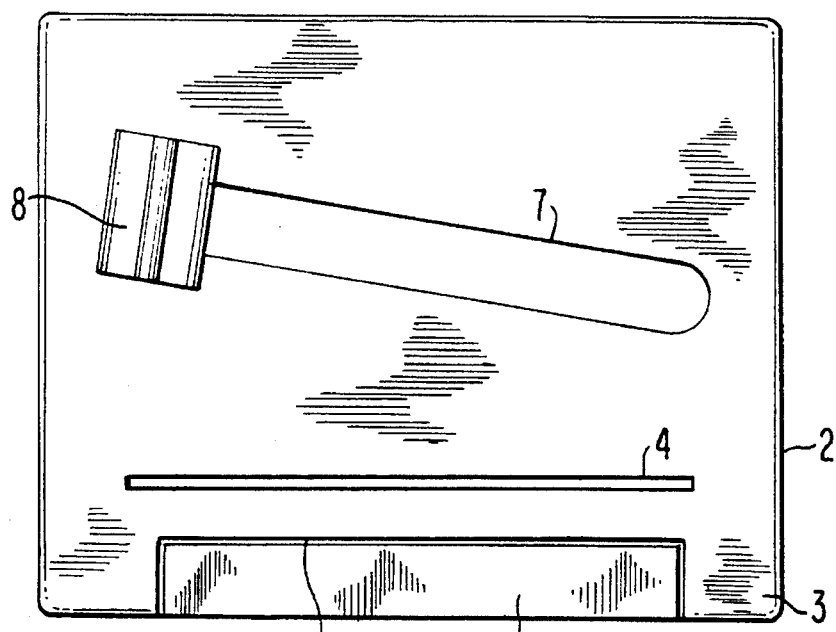
FIG. 1 is a plan view of the device for dispensing bandages in accordance with the present invention.
Figure 2:
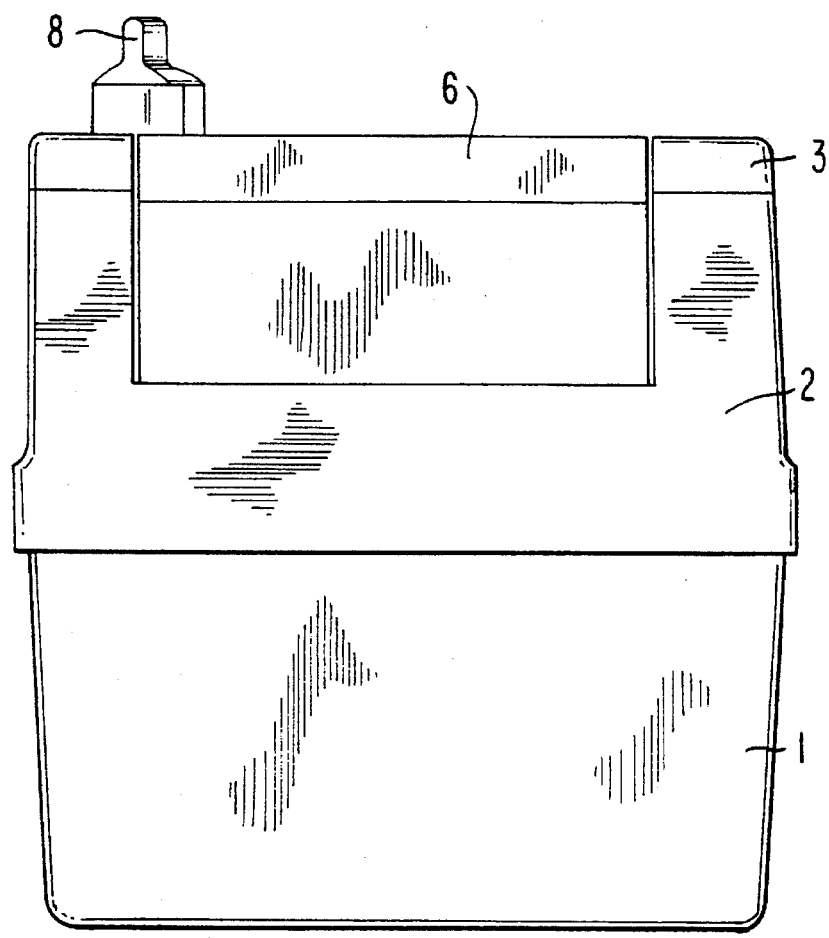
FIG. 2 is a front view of the device for dispensing bandages.

A device for dispensing bandages in accordance with the present invention has a lower supply container 1 for a material supply, for example a bandage material roll. An upper part 2 accommodating a cutting mechanism and an advancing mechanism for the bandage material is arranged on the supply container.

A cover 3 is turnably connected with the upper part by a hinge. The cover 3 is provided with a slot 4 for passing a piece of the bandage material to be cut off and also with a recess 5 for a pushbutton for advancing the bandage material. An inclined slot 7 is provided in the cover 3, and a handle 8 moves in the inclined slot 7 in the longitudinal direction of the slot.

Figure 3:
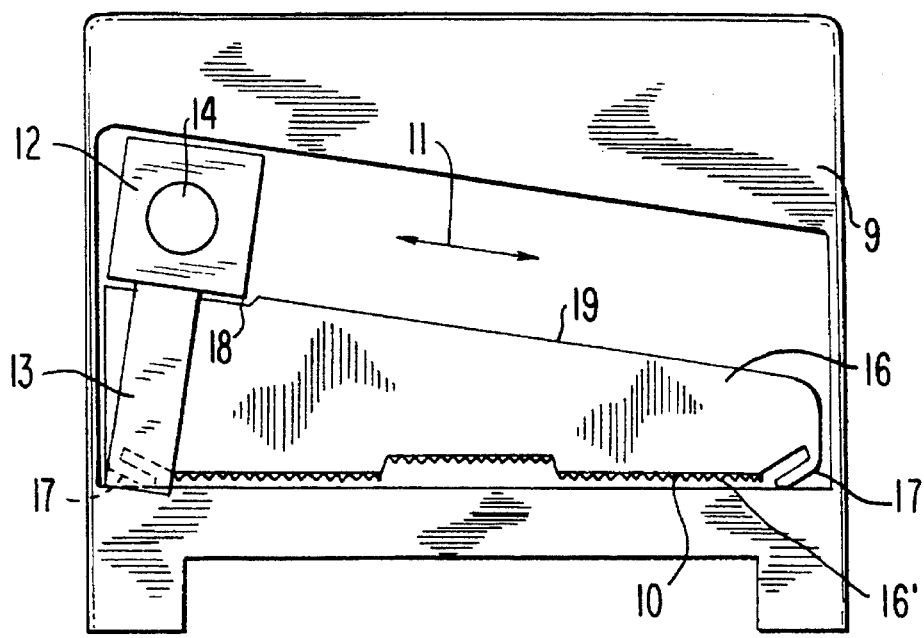
FIG. 3 is a plan view of the inventive device with a removed cover, exposing the cutting means of the device.

When the cover is lifted as shown in FIG. 3, the cutter guiding plate 9 can be seen under it. The lifting of the cover 3 from the upper part 2 is performed for example for exchanging cutters as will be explained hereinbelow.

A slightly conical groove 11 extends in the cutter guiding plate 9 at an angle relative to the slot 4 for advancing the bandage material. The angle of the groove 11 corresponds to the angle of the slot 7 shown in FIG. 1. A slider 12 of the cutting mechanism is movably arranged in the groove 11 and is formed as a cutter holder for a cutter 13.

A circular opening 14 is provided centrally in the cutter holder 12. It can be also conical and is seated on a corresponding conical part of the handle 8. During the longitudinal movement of the cutter holder 12 inside the groove 11, the cutter 13 forms a cut along a slot 10. The slot 10 has an expanded portion in its center so that a thicker part of the bandage material is not clamped during the advancement of the bandage material.

For performing an accurate cut, it is desirable to clamp the bandage material during its cutting in the slot 10. For this purpose a part 16 which is located at the opposite side of the groove 11 is moveable in the direction toward the slot 10 and provided with two springy projections on its opposite ends. Each projection 17 extends first towards the slot 10 and then substantially inclines relative to the slot towards its center. The opposite surface of the part 16 is provided with a recess 18. In the immovable position the cutter holder 12 is located inside the recess 18 of the part 16. When the cutter holder 12 is moved to the right, it moves out of the recess 18 onto an edge 19 of the part 16 and presses the part 16 toward the slot 10 so as to compress the projections 17 and to reduce the slot 10. Therefore, the portion of the bandage material located in the slot 10 is clamped, and the bandage material does not move during cutting.

The edge of the part 16 which faces the slot 10 is provided with a plurality of projections formed for example as small teeth 16'. When the part 16 is displaced by the cutter holder 12 toward the slot 10, the teeth 16' engage the bandage material and further improve clamping action so as to reliably hold the bandage material during cutting. It is understood that the handle can be connected with the cutter holder 12 directly and located under the cover 3.

Figure 4:
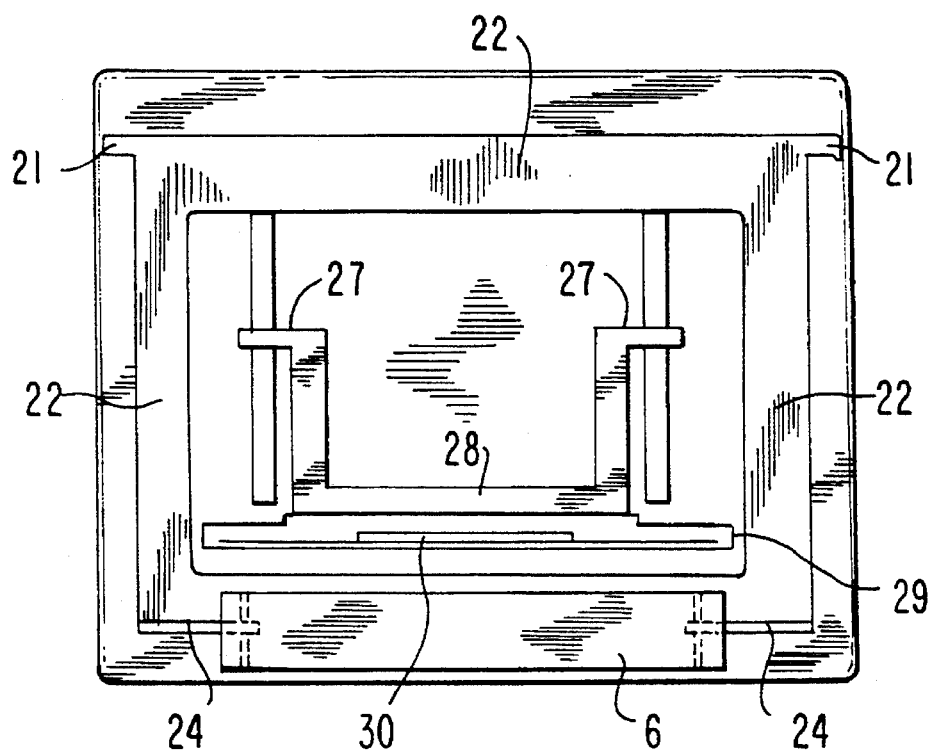
FIG. 4 is a plan view showing a frame and a driver of the bandage material advancing means.
Figure 5:
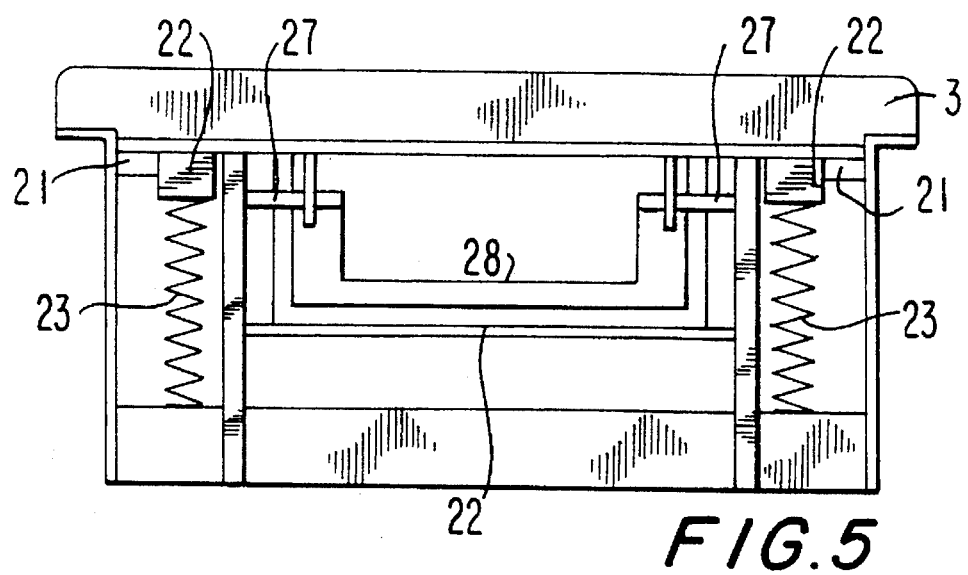
FIG. 5 is a rear view of the device for dispensing bandages in accordance with the present invention.
Figure 6:
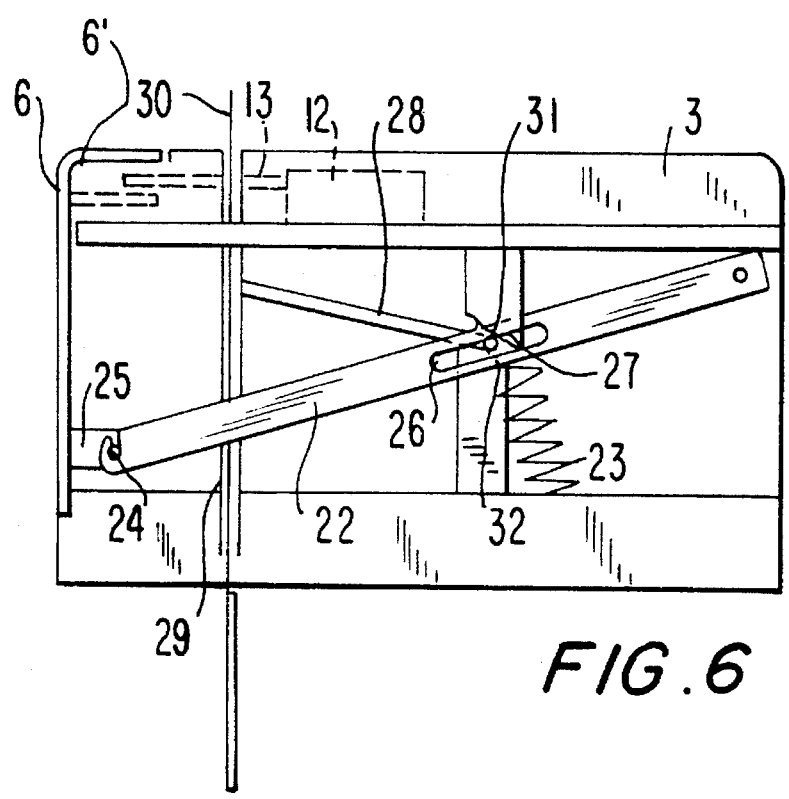
FIG. 6 is a view showing a section of the device for dispensing bandages in accordance with the present invention.

FIGS. 4–6 show an advancing mechanism for advancing the bandage material to be cut off. It includes a frame 22 which is turnably supported on two axles 21 in the housing wall of the upper part 2 under the cutter guiding plate 9. The frame 22 is turnable by the pushbutton 6 which is vertically movable before the slot 4 and 10 against the pressure springs 23 located under the frame 22. The frame 22 has two projections 24 which engage in corresponding recesses 25 in the pushbutton.

A driver 28 is arranged in the frame 22 and guided in the longitudinal slots 26 with two axle ends 27. By pressing the pushbutton down it is released and by the upward movement of the pushbutton 6 it abuts against the bandage material 30 in the guide 29 and displaces the bandage material in correspondence with the upward movement of the pushbutton by a piece upwardly so as to expose the bandage material from the slot 10 and 4. For this purpose, inside the upper part 2 two cams 31 and 32 are provided. They are located on the axles 27 and guided in correspondence with the downward and upward movement to provide the above mentioned effect.

It is understood that the advancing mechanism can be formed in a different way, for example by a roller or a further lifting mechanism. Finally, instead of the container 1, a roller arrangement for winding the bandage material can be provided.

When the cut has been performed and the required piece of the bandage material is cut off, the projections 17 relax and return the part 16 back to expand the slot 10 for further advancement of the bandage material.

It might happen that the person using the device retains the cutter holder in its final position. Therefore after the advancement of the next piece of the bandage material and an attempt to move the cutter holder the cutter having a cutting edge only on one of its sides cannot cut the bandage material with its dull side and the bandage material will be jammed. In order to avoid such situation, means is provided for blocking the advancing mechanism in the position when the cutter holder with the cutter is located in its final position. For this purpose the pushbutton 6 has a recess or a slot 6' (formed for example between a projection and a remaining part of the push button), and the cutter 13 in its final position engages in the slot as shown in FIG. 6. Therefore, the pushbutton 6 cannot be depressed for further advancement of the bandage material. Only when the cutter holder 12 with the cutter 13 is moved back to its initial position and the slot 6' is released, the pushbutton 6 can be again depressed to advance the bandage material.

Figure 7A:
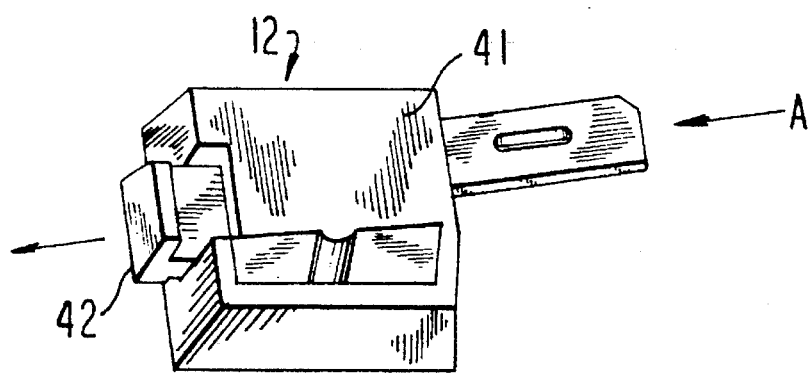
FIG. 7a is a view showing a cutter and a cutter holder of a cutting means of the invented device.
Figure 7B:
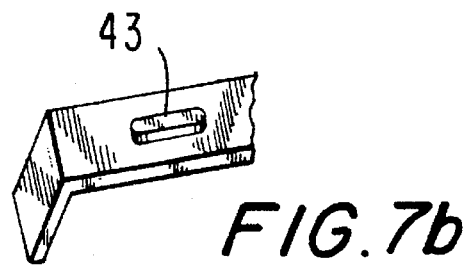
FIG. 7b is a view showing a removable part of the cutter holder from the bottom.
Figure 7C:
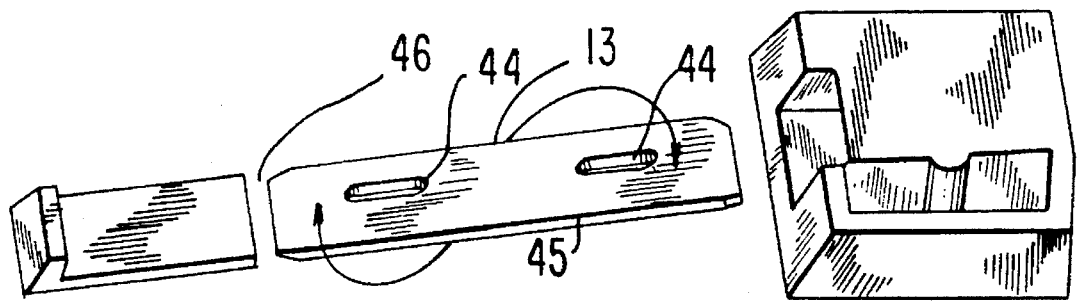
FIG. 7c is an exploded view of the cutter and the cutter holder of the cutting means.

FIGS. 7a–c show the details; of the cutting mechanism. The cutter holder 12 has a main part 41 and a removable part 42 which is insertable into a slot of the main part 41 and removable from the latter for exchanging the cutter 13. The removable part 42 has a projection 43 on its bottom side while the cutter 13 has two slots 44 spaced from one another in the direction of elongation of the cutter. Also, the cutter has two opposite cutting edges 45 and 46. In the assembled condition the projection 43 of the removable part 42 engages in one of the slots 44 of the cutter 13, for example the left slot in FIG. 7c and is inserted into the main part 41 so that a piece of the cutter extends outwardly beyond the part 41. In this condition, the cutter 13 cuts the bandage material with its one cutting edge. When this cutting edge is worn out and becomes dull, the cutter 13 is pushed in the direction of arrow A and due to the engagement between the projection 43 and the slot 44, pushes the removable part 42 to the left in FIG. 7a so that the removable part 42 together with the cutter 13 is removed from the main part 41. Then the blade can be turned 180°, and the projection 43 engages in another slot 44. In this position the removable part 42 together with the cutter 13 is inserted back into the main part 41, and after assembly of the device another cutting edge can be used for cutting the bandage material.

It is to be understood that when necessary a new cutter can be inserted into the cutting mechanism after the old cutter has been worn out and removed from the mechanism.

Figure 8:
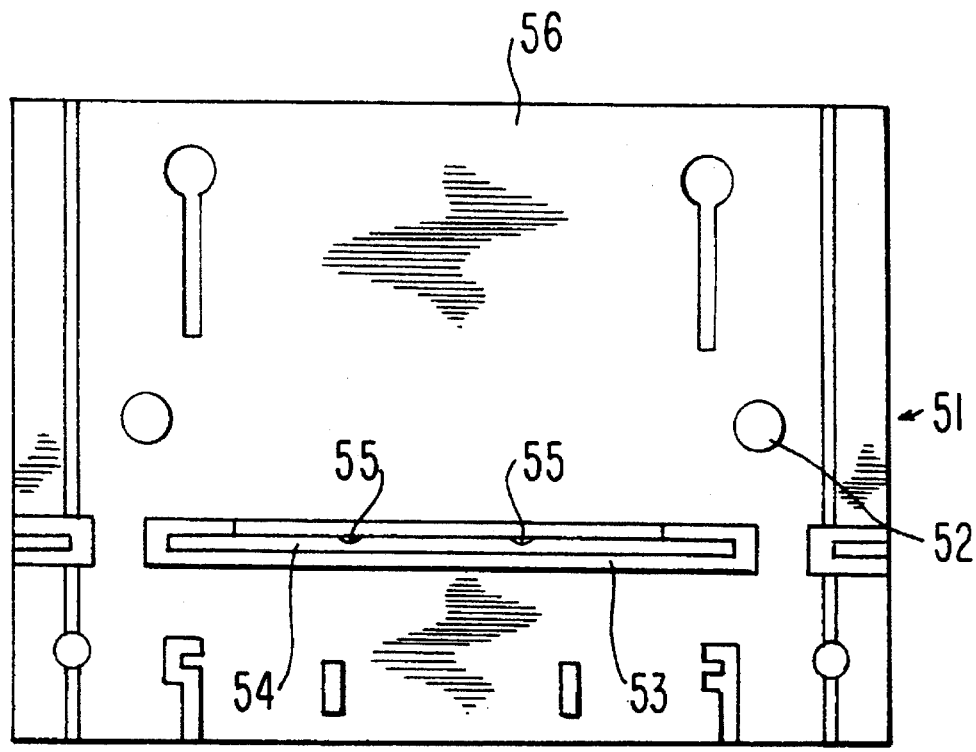
FIG. 8 is a plan view of a partition separating the bandage containing compartment from the rest of the device.
Figure 9:
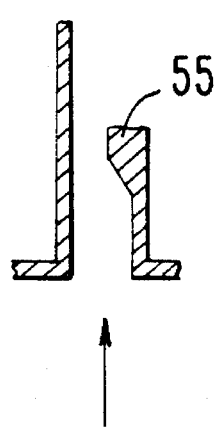
FIGS. 9 and 10 are views showing two modifications of retaining formations for the bandage material.
Figure 10:
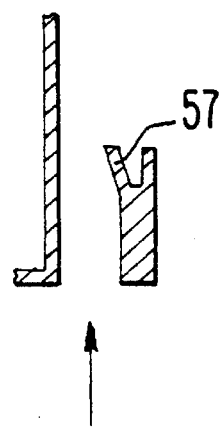

FIG. 8 shows a plan view of a partition 51 which separates a bandage material accommodating compartment from the rest of the device. The bandage material is located under the partition 51. The partition 51 is formed as a plate. It is provided with two projections 52 which form centering pins for the springs 23. A vertical wall 53 extends vertically upwardly from the base plate 56 of the partition 51 and forms a closed passage 54 through which the bandage material is to be transported upwardly. Two cams 55 are provided on the wall 53 at one side of the slot 54 as shown in FIG. 9. They apply a certain pressure to the bandage material and keep the bandage material in an upright position to prevent its falling back into the bandage material accommodating compartment. Instead of the cams, springs 57 can also be provided on the wall 53 at one side of the slot 54 and formed as barbs, as shown in FIG. 10.

It will be understood that each of the elements described above, or two or more together, may also find a useful application in other types of constructions differing from the types described above.

While the invention has been illustrated and described as embodied in a device for dispensing bandages and the like, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed and desired to be protected by Letters Patent is set forth in the appended claims:

1. A device for dispensing a bandage material, comprising a container for accommodating a supply of the bandage material; means for advancing the bandage material from said container so as to expose a desired piece of the bandage material outside of said container; and means for cutting the exposed piece of the bandage material, said cutting means including a cutting element movable between an initial position before cutting the piece of the bandage material and a final position after the piece of the bandage material has been cut off during which movement from said initial position to said final position the piece of the bandage material is being cut; and means for preventing advancement of the bandage material by said advancing means when said cutting element is in said final position, said preventing means cooperating with said advancing means so that in said final position said advancing means cannot advance the bandage material outside said container.

2. A device as defined in claim 1, wherein said advancing means include an advancing element movable in a predetermined direction to advance the bandage material, said preventing means including means extending from said cutting means and blocking the movement of said advancing element in said predetermined direction when said cutting element is in said final position.

3. A device as defined in claim 2, wherein said advancing element has a recess, said preventing means being a portion of said cutting element engaging in said recess in said final position of said cutting element.

4. A device as defined in claim 1; and further comprising means forming a slot through which the bandage material is advanced by said advancing means, and a movable guide which is displaceable towards said slot during movement of said cutting element from said initial position to said final position so as to reduce said slot and to clamp the bandage material during cutting, said movable guide being provided with elastic projections which are compressed during displacement of said movable guide towards said slot during movement of said cutting element from said initial position to said final position, and then displace the movable guide back when said cutting element is again in the initial position.

5. A device as defined in claim 4, wherein said movable guide has two ends, said elastic projections being located at said ends of said movable guide and extend first in direction toward said slot transverse to said slot and then are inclined in direction substantially toward a center of said slot.

6. A device as defined in claim 4, wherein said movable guide has an edge which faces toward said slot and is provided with a plurality of small projections engageable with said bandage material so as to firmly hold the bandage material during cutting.

7. A device as defined in claim 6, wherein said small projections are formed by a plurality of small teeth.

8. A device as defined in claim 1, wherein said cutting means include a cutter and a cutter holder which holds said cutter, said cutter holder having a main part and a removable part which engages said cutter and is insertable into said main part and removable from said main part.

9. A device as defined in claim 8, wherein said removable part has an engaging projection, said cutter being elongated and having two slots spaced from one another in the direction of elongation and alternatingly engageable with said projection.

10. A device as defined in claim 9, wherein said cutter has two opposite cutting edges extending along said cutter and spaced from one another in a direction transverse to the direction of elongation so that said cutter is engaged by said projection of said removable part in one position in which one of said cutting edges in an assembled condition of the device cuts the bandage material, and then is turned over and engaged with said removable part in another position in which another of said cutting edges in the assembled condition cuts the bandage material.

11. A device as defined in claim 1, further comprising a partition subdividing said container into a bandage material accommodating compartment and a cutting means accommodating compartment, said partition having a slot through which the bandage material is supplied from said bandage material accommodating compartment into said cutting means accommodating compartment, said slot having at least one wall provided with at least one projection for engaging the bandage material and preventing falling back of the bandage material into said bandage material accommodating compartment.

12. A device as defined in claim 11, wherein said at least one projection is formed as a cam applying a pressing force against said bandage material.

13. A device as defined in claim 11, wherein said at least one projection is formed as a spring applying a pressing force against the bandage material.

* * * * *